(12) United States Patent
Sanders et al.

(10) Patent No.: US 6,497,135 B1
(45) Date of Patent: Dec. 24, 2002

(54) CONTROLLER FOR USE WITH WIDE RANGE OXYGEN SENSOR

(75) Inventors: Stephen Paul Sanders, Millington, MI (US); Peter James Maloney, New Hudson, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/658,436

(22) Filed: Sep. 8, 2000

(51) Int. Cl.$^7$ ........................ G01N 27/12; G01N 27/419
(52) U.S. Cl. ...................... 73/23.2; 73/23.31; 73/23.32; 123/693; 123/694
(58) Field of Search ............................... 73/23.2, 23.31, 73/23.32; 123/694, 693, 695

(56) References Cited

U.S. PATENT DOCUMENTS

| | | | |
|---|---|---|---|
| 4,306,444 A | * 12/1981 | Hattori et al. | 73/23.32 |
| 4,519,237 A | * 5/1985 | Kubo | 73/23.31 |
| 4,526,147 A | * 7/1985 | Grob | 123/694 |

* cited by examiner

*Primary Examiner*—Daniel S. Larkin
(74) *Attorney, Agent, or Firm*—Vincent A. Cichosz

(57) ABSTRACT

A voltage sensing system that has a pair of input leads having a first input lead, and a second input lead each sensing a non-grounded voltage, and an amplifier coupled to the pair of input leads, the amplifier generating an amplifier output voltage in response to a voltage on the first input lead, a voltage on the second input lead and an offset voltage. The system further includes a controller for receiving the amplifier output voltage and determining an operating range, and an offset voltage generator for generating the offset voltage, the offset voltage generator altering the offset voltage in response to the operating range determined by the controller. An oxygen sensing system using a sample resistance for sensing a bi-directional current may be coupled to the voltage sensing system. A method for sensing air-to-fuel ratio includes sampling an input voltage drop derived from a pumping current across a sampling resistance. The input voltage is indicative of air-to-fuel ratio. The input voltage drop is amplified in response to an offset voltage to generate an amplified output voltage indicative of air-to-fuel ratio. An operating range is determined in response to the amplified output voltage. The offset voltage is then adjusted in response to the operating range.

9 Claims, 3 Drawing Sheets

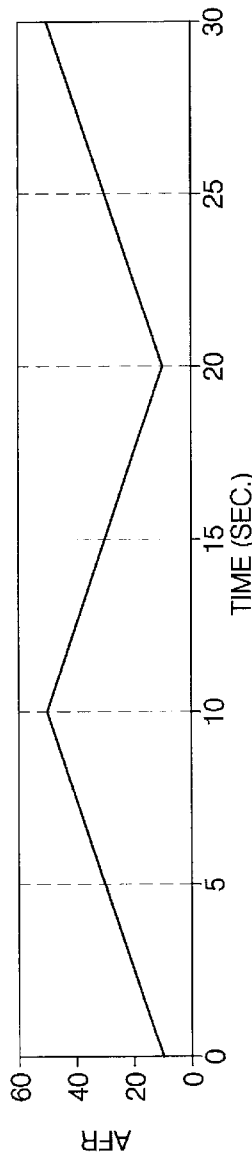
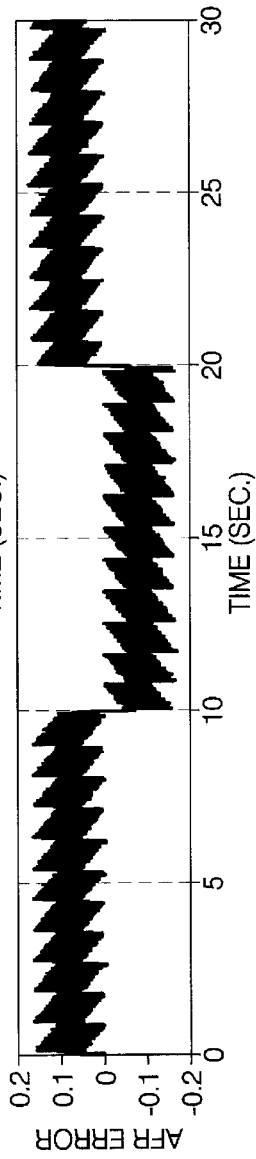
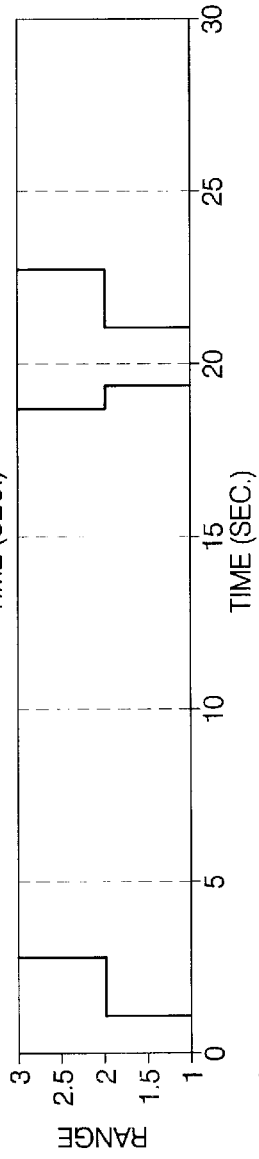
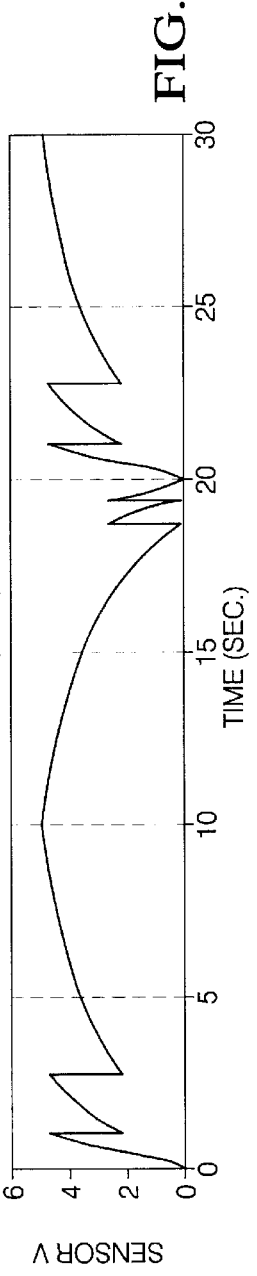
FIG. 3A
FIG. 3B
FIG. 3C
FIG. 3D

CONTROLLER FOR USE WITH WIDE RANGE OXYGEN SENSOR

TECHNICAL FIELD

The invention relates to a controller for use with a wide range oxygen sensor.

BACKGROUND OF THE INVENTION

Oxygen sensors are used in a variety of applications that require qualitative and quantitative analysis of gases. For example, oxygen sensors have been used for many years in automotive vehicles to sense the presence of oxygen in exhaust gases, such as when an exhaust gas content switches from rich to lean or lean to rich. In automotive applications, the direct relationship between oxygen concentration in the exhaust gas and the air-to-fuel ratio of the fuel mixture supplied to the engine allows the oxygen sensor to provide oxygen concentration measurements for determination of optimum combustion conditions, maximization of fuel economy, and the management of exhaust emissions.

Wide range oxygen sensors are known in automotive applications which can measure air-to-fuel ratios ranging from 9 to 50, for example. It is known to use a controller for processing signals derived from an oxygen sensor. When a controller is calibrated to operate over the entire wide air-to-fuel range (e.g., 9 to 50), there is insufficient sensitivity in the region around stoiciometry (e.g., air-to-fuel ratio of 14.7). The lack of sensitivity is due to the use of an analog to digital converter for converting the output of the oxygen sensor to a digital value. To obtain a higher sensitivity, a high-resolution analog to digital (A/D) converter is needed. The cost associated with the A/D in a high-resolution context is high. In addition, the A/D converter may take up valuable space as well. Thus, high-resolution A/D converters are not well suited for automotive applications. Therefore, a separate system, or subsystem, that provides more precise air/fuel ratio data is desirable.

BRIEF SUMMARY OF THE INVENTION

A voltage sensing system that has a pair of input leads having a first input lead, and a second input lead each sensing a non-grounded voltage, and an amplifier coupled to the pair of input leads, the amplifier generating an amplifier output voltage in response to a voltage on the first input lead, a voltage on the second input lead and an offset voltage. The system further includes a controller for receiving the amplifier output voltage and determining an operating range, and an offset voltage generator for generating the offset voltage, the offset voltage generator altering the offset voltage in response to the operating range determined by the controller.

An oxygen sensing system using a sample resistance for sensing a bi-directional current coupled to the voltage sensing system.

A method for sensing air-to-fuel ratio including sampling an input voltage drop derived from a pumping current across a sampling resistance. The input voltage is indicative of air-to-fuel ratio. The input voltage drop is amplified in response to an offset voltage to generate an amplified output voltage indicative of air-to-fuel ratio. An operating range is determined in response to the amplified output voltage. The offset voltage is then adjusted in response to the operating range.

BRIEF DESCRIPTION OF THE DRAWINGS

The apparatus and method will now be described by way of example, with reference to the accompanying drawings, which are meant to be exemplary, not limiting.

FIGS. 3a, 3b, 3c, and 3d are a set of time lines in relation to various parameters.

DETAILED DESCRIPTION OF THE INVENTION

Figure 1:
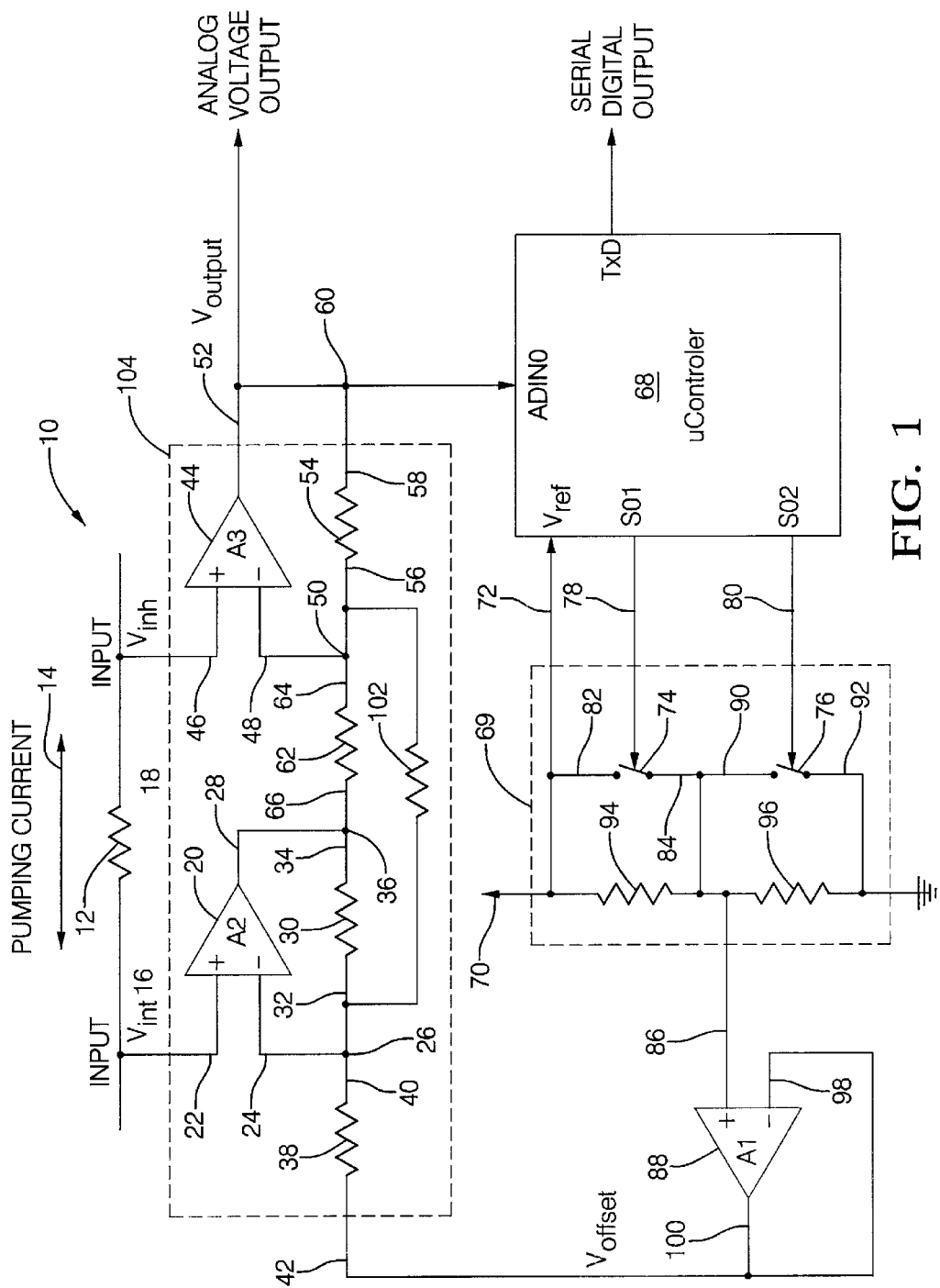
FIG. 1 depicts a circuitry that is one embodiment of the instant invention.

FIG. 1 depicts a circuit 10 for use with a wide range oxygen sensor having automatic operating range switching. Referring to FIG. 1, a current sensing resistance 12 senses a bi-directional pumping current 14 generated by an oxygen sensor as is known in the art. The sensing resistance 12 has a first lead 16 and a second lead 18. The bi-directional pumping current 14 may flow through the sensing resistance 12 either from the first lead 16 to the second lead 18, or vice versa. In other words, dependent upon external conditions, such as an oxygen sensor generating the bi-directional pumping current 14, the voltage drop may have opposite polarity from the first lead 16 to the second lead 18. The first lead 16 is coupled to a second operational amplifier 20. The second operational amplifier 20 has two input leads, a non-inverting lead 22 that is connected to the first lead 16, and an inverting lead 24 that is coupled to a first node 26. In addition, the second operational amplifier 20 further includes an output lead 28. A resistance 30 has a first lead 32 and a second lead 34. The first lead 32 is coupled to the first node 26. The second lead 34 is coupled to the output lead 28 of the second operational amplifier 20 by way of a second node 36. Furthermore, a resistance 38 has a first lead 40 and a second lead 42. The first lead 40 is coupled to the first node 26.

Similarly, the second lead 18 is coupled to a third operational amplifier 44. The third operational amplifier 44 has two input leads, a non-inverting lead 46 that is connected to the second lead 18, and an inverting lead 48 that is coupled to a third node 50. In addition, the third operational amplifier 44 further includes an output lead 52. A resistance 54 has a first lead 56 and a second lead 58. The first lead 56 is coupled to the first node 50. The second lead 58 is coupled to the output lead 52 of the third operational amplifier 44 by way of a fourth node 60. Furthermore, a resistance 62 has a first lead 64 and a second lead 66. The first lead 64 is coupled to the first node 50. The second lead 66 is coupled to the second node 36. Furthermore, the fourth node 60 forms an output of the circuit 10, as well as a starting point for a feedback loop to a controller 68 wherein the analog signal of the fourth node is converted to a digital signal therein. The digital signal is indicative of the air-to-fuel ratio, which determines the bi-directional pumping current 14. The controller 68 may be the automobile main controller or may be a sensor controller which outputs the digital signal for further processing. The controller 68 is powered by a positive power source 70 via line 72. In addition, the controller 68 controls two switches, 74 and 76 in an offset voltage generator 69 via line 78 and line 80, respectively. Switch 74 has a first end 82 and a second end 84. The first end 82 is coupled to the positive power source 70. The second end 84 is coupled to a non-inverting input 86 of a first operational amplifier 88. Switch 76 has a first end 90 and a second end 92. The first end 90 is coupled to the non-inverting input 86 of the first operational amplifier 88. The second end 92 is coupled to ground. A third resistance 94 couples between the first end 82 and the second end 84 of switch 74. Similarly, a fourth resistance 96 couples between the first end 90 and the second end 92 of switch 76. The first operational amplifier 88 further has an inverting input 98, and an output 100. The inverting input 98 and the output 100 are electrically connected thereby forming a voltage-follower, which is known in the art. In other words, the first operational amplifier 88 is being used as a voltage-follower that generates or outputs an offset voltage, which is coupled or exerts the offset voltage upon the second lead 42 of resistance 38. Furthermore, a straddling resistance 102 has a first lead coupled to the first node 26 and a second lead coupled to the third node 50. It is noted that the operational amplifiers 20 and 44, together with resistances 38, 30, 54, 62, as well as resistance 102 form a composite amplifier 104.

The sensing resistance 12 detects the bi-directional current 14, such as an oxygen pumping current that is the measure of an oxygen partial pressure of an exhaust. The differential voltage developed across sensing resistance 12 is amplified and converted to a single-ended, ground-referenced voltage by a composite amplifier comprising the second amplifier 20 and the third amplifier 44. The output voltage at the output end 52 can be formulated as $$Voutput = (Vinh - Vinl) * [1 + R1/R2 + 2*R1/Rg] + Voffset$$

where:
- R1 = resistance 38 = resistance 54,
- R2 = resistance 30 = resistance 62,
- Vinh is the high voltage at one end of the sensing resistance 12 in relation to
- Vinl, which is the low voltage at the other end of the sensing resistance 12,
- Voffset is the offset voltage, and
- Rg is the straddling resistance 102.

As can be appreciated, the relationship between the Voffset and the rest of the elements of the Voutput equation can be adjusted by suitably choosing the values of resistances 30, 38, 54, 62, and 102. Furthermore, the voltage difference across sensing resistance 12, which is depended upon a type of oxygen sensor, is significant as well. It should be noted that the value of output voltage Voutput affects the determination of the offset voltage Voffset as described herein.

In addition, the offset voltage component of the above equation, Voffset at the second lead 42, may be determined by an algorithm executed by controller 68. Controller 68 includes output ports coupled via line 78 and 80, respectively, to activate either one, or neither of switches 74 and 76. The algorithm may be constructed into software 1 embedded into a machine, such as a computer. The resulting offset voltage is buffered by the operational amplifier 88 and coupled to amplifier 104. In other words, the resulting offset voltage is connected to the offset voltage input of the composite amplifier. The following is one example of the algorithm executed by the controller 68:

```
;;;Implement Automatic Output Range Switching:
    INPUT ADIN4
    Vout=ADIN4
    SET_F_CENTER_RANGE; INITIAL ASSUMPTION
;;;Center Operating Range:
    If (F_CENTER_RANGE) Then,
    If (Vout>4.75V) Then,
    Clear F_CENTER_RANGE
    Set F-LEAN-RANGE
    Else If (Vout<0.25V),
    Clear F_CENTER-RANGE
    Set F_RICH RANGE
    End If
;;;Lean Operating Range:
    Else If (F_LEAN_PANGE) Then,
    If (Vout>4.75V) Then,
    Set F_OUT_OF_RANGE_LEAN
       Else If (Vout<0.25V),
       Clear F_LEAN_RANGE
       Set F_CENTER RANGE
    End If
;;;Rich Operating Range:
    Else If (F_RICH_RANGE) Then,
    If (Vout>4.75V) Then,
    Clear F RICH RANGE
    Set F_CENTER_RANGE
    Else If (Vout<0.25V),
    Set F_OUT_OF_RANGE_RICH
    End If
End If
```

When the controller 68 determines that the system must operate in the rich exhaust region, switch 74 is closed, and switch 76 is open thus connecting the supply voltage 70 to the input of buffer 88. The result is that an offset voltage Voffset equal to Vcc 70 is obtained. For example, Vcc may equal to 5 volts.

When the controller 68 determines that the system must operate in the center region or in the region around stoiciometry (e.g. A/F=14.7), switches 76 and 74 are both opened allowing the offset voltage to be determined by the voltage divider formed by resistors 94 and 96. If 94 and 96 are of the same value, the resulting offset voltage will be half of the supply voltage (2.50V for Vcc=5.0V, for example).

When the controller 68 determines that the system must operate in the lean exhaust region, switch 74 is opened, and switch 76 is closed. The result is that a grounding of the input of buffer 88 occurs, which results in an offset voltage Voffset equal to ground (i.e., OV).

During the controller initialization procedure, an initial assumption is made that the system is operating in the center range (The flag, F_CENTER_RANGE, is set). Following initialization, the automatic range switching algorithm detailed above is executed by controller 68 at a regular sampling interval to cause the output range to switch when required.

Figure 2:
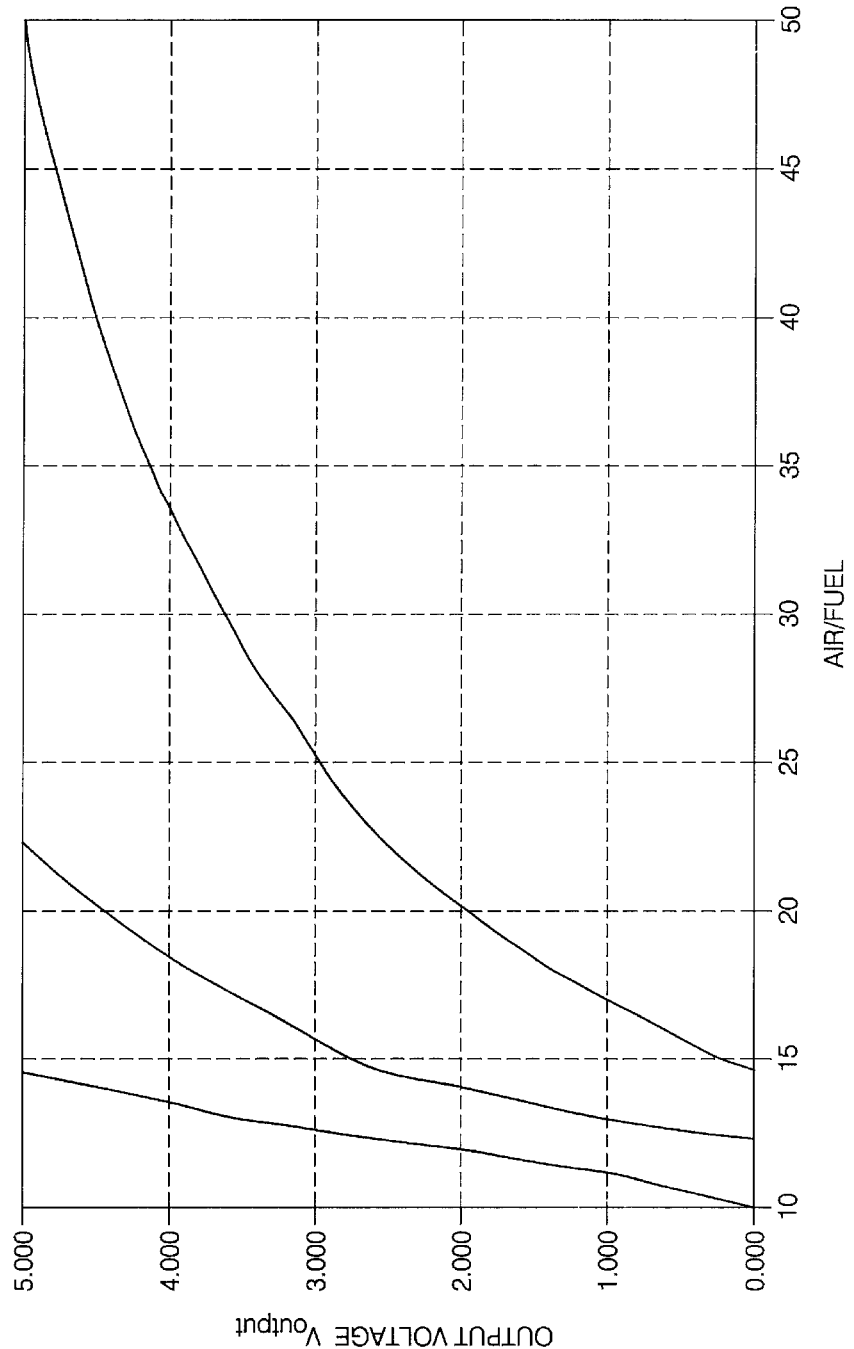
FIG. 2 shows the relationship between the air fuel ratio and the output voltage of the circuitry.

Referring to FIG. 2, the relationship between the output voltage Voutput and air/fuel ratio is depicted. As shown in FIG. 2, in the rich mode (i.e., low air-to-fuel ratio) if the output voltage Voutput exceeds a limit (e.g., 4.75 volts), the controller 68 switches modes to the center operating region by adjusting the offset voltage as described above. Switching from the rich range to the center range alters the slope in the plot of output voltage vs. air-to-fuel ratio and allows controller 68 to provide more accurate A/D conversion of the output voltage Voutput. In the center operating range, the controller 68 switches to the rich operating mode if the output voltage is below a lower limit (e.g., 0.25 volts) and switches to the lean operating mode if the output voltage is above an upper limit (e.g., 4.75 volts). Again, this alters the slope in the plot of output voltage vs. air-to-fuel ratio and provides more accurate A/D) conversion of the output voltage Voutput. In the lean operating mode (i.e., high air-to-fuel ratio), the controller 68 switches modes to the center operating region by adjusting the offset voltage as described above if the output voltage is below a lower limit (e.g., 0.25 volts). Switching from the lean range to the center range alters the slope in the plot of output voltage vs. air-to-fuel ratio and allows controller 68 to provide more accurate A/D conversion of the output voltage Voutput.

FIG. 3a is a plot of air-to-fuel ratio (AFR) versus time. FIG. 3b is a plot of AFR error versus time corresponding to the AFR in FIG. 3a. FIG. 3c is a plot of range (e.g. rich, center, and lean) versus time for the AFR of FIG. 3a. FIG. 3d is a plot of Voutput versus time for the AFR of FIG. 3a.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is being claimed is:

1. A voltage sensing system, comprising:

a pair of input leads having a first input lead and a second input lead each sensing a non-grounded voltage;

an amplifier coupled to said pair of input leads, said amplifier generating an amplifier output voltage in response to a voltage on said first input lead, a voltage on said second input lead, and an offset voltage, a controller for receiving said amplifier output voltage and determining an operating range; and an offset voltage generator for generating said offset voltage, said offset voltage generator altering the offset voltage in response to said operating range determined by said controller.

2. The voltage sensing system of claim 1, wherein said non-grounded voltage is derived from a current sampled by a sampling resistance.

3. The voltage sensing system of claim 1, wherein said amplifier comprises a first operational amplifier, and a second operational amplifier.

4. The voltage sensing system of claim 1, wherein said offset voltage generator comprises a voltage divider.

5. An oxygen sensing system, comprising:

a sensing resistance having a first end and a second end for sensing a bi-directional current and;

a voltage sensing system sensing a voltage indicative of oxygen, having:

a pair of input leads coupled to said first end and said second end, respectively, said pair of input leads comprising a first input lead and a second input lead each sensing a non-grounded voltage;

an amplifier coupled to said pair of input leads, said amplifier generating an amplifier output voltage in response to a voltage on said first input lead, a voltage on said second input lead, and an offset voltage;

a controller for receiving said amplifier output voltage and determining an operating range; and an offset voltage generator for generating said offset voltage, said offset voltage generator altering the offset voltage in response to said operating range determined by said controller.

6. The oxygen sensing system of claim 5, wherein said amplifier comprises a first operational amplifier and a second operational amplifier.

7. The oxygen sensing system of claim 5, wherein said offset voltage generator comprises a voltage divider.

8. The oxygen sensing system of claim 5, wherein said operating range is one of a set of ranges corresponding to a set of different concentrations of oxygen.

9. The oxygen sensing system of claim 8, wherein said set of ranges comprises three different ranges.

* * * * *